US008852464B2

(12) United States Patent
Soghomonian et al.

(10) Patent No.: US 8,852,464 B2
(45) Date of Patent: Oct. 7, 2014

(54) ELECTRICALLY CONDUCTING MICROPOROUS FRAMEWORKS

(75) Inventors: Victoria Soghomonian, Blacksburg, VA (US); Jean J. Heremans, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 820 days.

(21) Appl. No.: 13/128,452

(22) PCT Filed: Nov. 10, 2009

(86) PCT No.: PCT/US2009/063896
§ 371 (c)(1), (2), (4) Date: May 10, 2011

(87) PCT Pub. No.: WO2010/054383
PCT Pub. Date: May 14, 2010

(65) Prior Publication Data
US 2011/0210294 A1     Sep. 1, 2011

Related U.S. Application Data

(60) Provisional application No. 61/112,848, filed on Nov. 10, 2008.

(51) Int. Cl.
| | | |
|---|---|---|
| *H01B 1/00* | (2006.01) | |
| *H01B 1/02* | (2006.01) | |
| *H01B 1/12* | (2006.01) | |
| *C01G 28/02* | (2006.01) | |
| *C01G 33/00* | (2006.01) | |
| *H02J 7/00* | (2006.01) | |
| *H01G 11/46* | (2013.01) | |
| *C07F 9/68* | (2006.01) | |
| *H01G 11/24* | (2013.01) | |
| *H01G 11/30* | (2013.01) | |

(52) U.S. Cl.
CPC *C07F 9/68* (2013.01); *H01G 11/46* (2013.01); *H01G 11/24* (2013.01); *H01G 11/30* (2013.01); *Y02E 60/13* (2013.01)
USPC ............ 252/519.1; 252/500; 423/594.8; 423/601; 423/602; 320/167

(58) Field of Classification Search
USPC ............ 252/500, 519.1; 423/594.8, 601, 602; 320/167
See application file for complete search history.

(56) References Cited

FOREIGN PATENT DOCUMENTS

WO     2008118422 A1     10/2008

OTHER PUBLICATIONS

Krasil'nikov et al. Loss of Activity by Vanadium Sulfuric Acid Catalysts under the Action of Arsenic (III) Oxide Vapor. Russian Journal of Applied Chemistry. 2006. vol. 79, No. 4, 619-623.*
Zhao, et al., "Hydrothermal synthesis, structure and catalytic property of a novel open-framework oxovanadium arsenate," Journal of Materials Chemistry, 2001, pp. 1553-1554, vol. 11, The Royal Society of Chemistry, London, UK.
Bu, et al., "A three-dimensional neutral framework of a novel decavanadium cluster bridged by an AsO4 tetrahedron . . . ," Chemical Communications, 2000, pp. 1279-1280, The Royal Society of Chemistry, London, England.
Hou, et al., "A novel one-dimensional arsenic vanadate decorated with a transition metal complex . . . ," Journal of Molecular Structure, 2004, pp. 81-88, vol. 689, Elsevier, Maryland Heights, MO, USA.
Zheng, et al., "Hydrothermal Synthesis and Structural Characterization of Two Novel Arsenic-Vanadium Clusters . . . ," Journal of Cluster Science, Mar. 2005, pp. 23-37, vol. 16, No. 1, Springer, New York, NY, USA.
Haushalter, et al., "Hydrothermal Synthesis and Structural Characterization of the Two New Vanadium Arsenates . . . ," Chemistry of Materials, Sep. 1994, p. 1463, vol. 6, No. 9, American Chemical Society, Washington, DC, USA.

* cited by examiner

*Primary Examiner* — Harold Pyon
*Assistant Examiner* — Tanisha Diggs
(74) *Attorney, Agent, or Firm* — Blank Rome LLP

(57) ABSTRACT

Electrically conducting vanadium arsenate or vanadium phosphate materials are described. The materials include a vanadium arsenate or vanadium phosphate framework structure about organic template and water molecules which may be removed to leave a microporous structure. The three-dimensional vanadium framework may provide electronic conductivity, while the extra-framework constituents may provide ionic conductivity.

14 Claims, 6 Drawing Sheets

US 8,852,464 B2

ELECTRICALLY CONDUCTING MICROPOROUS FRAMEWORKS

STATEMENT OF GOVERNMENT INTEREST

The subject matter of this application was made with support from the United States Government under Grant No. DMR-0943971 from the National Science Foundation. The United States Government has certain rights in the invention.

STATEMENT OF PRIORITY

This application claims the benefit of U.S. Provisional Patent Application Ser. No. 61/112,848, filed Nov. 10, 2008, the disclosure of which is hereby incorporated in its entirety by reference herein.

FIELD OF THE INVENTION

This invention relates to organically templated three-dimensional framework compositions consisting of transition metal polyhedra with arsenate or phosphate tetrahedra, particularly vanadium-containing compositions, and properties and uses thereof.

BACKGROUND OF THE INVENTION

Electrically conducting zeotype frameworks offer a new approach to energy storage technologies. In particular they offer new opportunities in electrical charge storage applications, such as in ultracapacitors, battery electrodes, and ion conducting membranes. Tailored materials with mono-dispersed pore size distribution and large pore density per unit volume have the potential to provide optimal electrical energy storage, in terms of both energy density and power density.

High-surface-area activated carbonaceous materials are most often used for electrical energy storage, but these materials possess random pore sizes and broad distributions leading to sub-optimal charge packing. Nano-carbon material promises better pore size and distribution over mesoporous carbon, but has proved difficult to produce in bulk. While nanostructured materials such as zeolites show more efficient packing than the above materials, they have previously been produced only in electrically insulating forms.

The development of different options for improving electrical energy storage capabilities is essential to meet the current and future requirements for efficient use of electrical energy in applications. New materials are needed to improve charge storage capabilities by increasing both the energy and the power densities, as well as achieving faster recharge times. Electrically conducting framework materials are crucial to the development of new charge storage materials. Porous electrically conducting frameworks allow for high storage densities and for new strategies in which materials simultaneously exploit multiple charge storage and mobility mechanisms. Particularly desirable are microporous zeotype electrically conducting frameworks where pore sizes range from sub-nanometer to 2 nm, and are roughly the size of hydrated and/or solvated ions and small molecules.

Ultracapacitors are of particular interest in the field of electrical energy storage devices. The capacitance of the electrical double-layer (EDLC) forms the basis for ultracapacitors, where the layer is formed between mobile ions in an electrolyte and an electrically conducting plate. The capacitance per unit area is high, due to the short charge separation distance characteristic of ionic double-layers typically atomic in scale. The high attainable capacitance forms the basis for widespread similar electrolytic capacitors. An ultracapacitor adds to this a large effective area of the capacitor plate by employing a porous conducting medium as electrode. The capacitance values correlate with pore dimension and ion size, with pore size distribution, and pore density per unit volume. Thus an electrically conducting microporous zeotype material would function as an ultracapacitor material. A conducting zeotype material may also have additional uses as a novel semiconductor material for electronics and optics applications, in addition to properties and applications already known for zeolites and zeotypes such as catalysis, sorption, separation, ion-exchange membranes, etc.

Therefore, there is a need in the art for the development of conducting microporous zeotype materials for use as ultracapacitors in energy storage applications.

SUMMARY OF THE INVENTION

It is an object of the present invention to provide electrically conductive compositions having a vanadium arsenate or vanadium phosphate framework with tunnels and cavities. The tunnels and cavities of the frameworks of the compositions of the present invention may house water molecules and/or organic cations. The water molecules and organic cations may also be replaced, either in whole or in part, by inorganic cations.

It is a further object of the present invention to provide methods for synthesizing electrically conductive compositions having a vanadium arsenate or vanadium phosphate framework. The methods of the present invention involve the mixing of vanadate with arsenate or phosphate reagents, organic template, water, and optionally an acid.

It is a still further object of the present invention to provide media for charge storage applications, chemical catalysis, adsorption and separation reactions containing the compositions of the present invention. The compositions of the present invention can provide greater energy density for capacitors, ultracapacitors, battery electrodes, and ion conducting membranes. The compositions are also useful for novel memory and electronic and/or optoelectronic devices.

DETAILED DESCRIPTION OF THE INVENTION

Figure 1A:
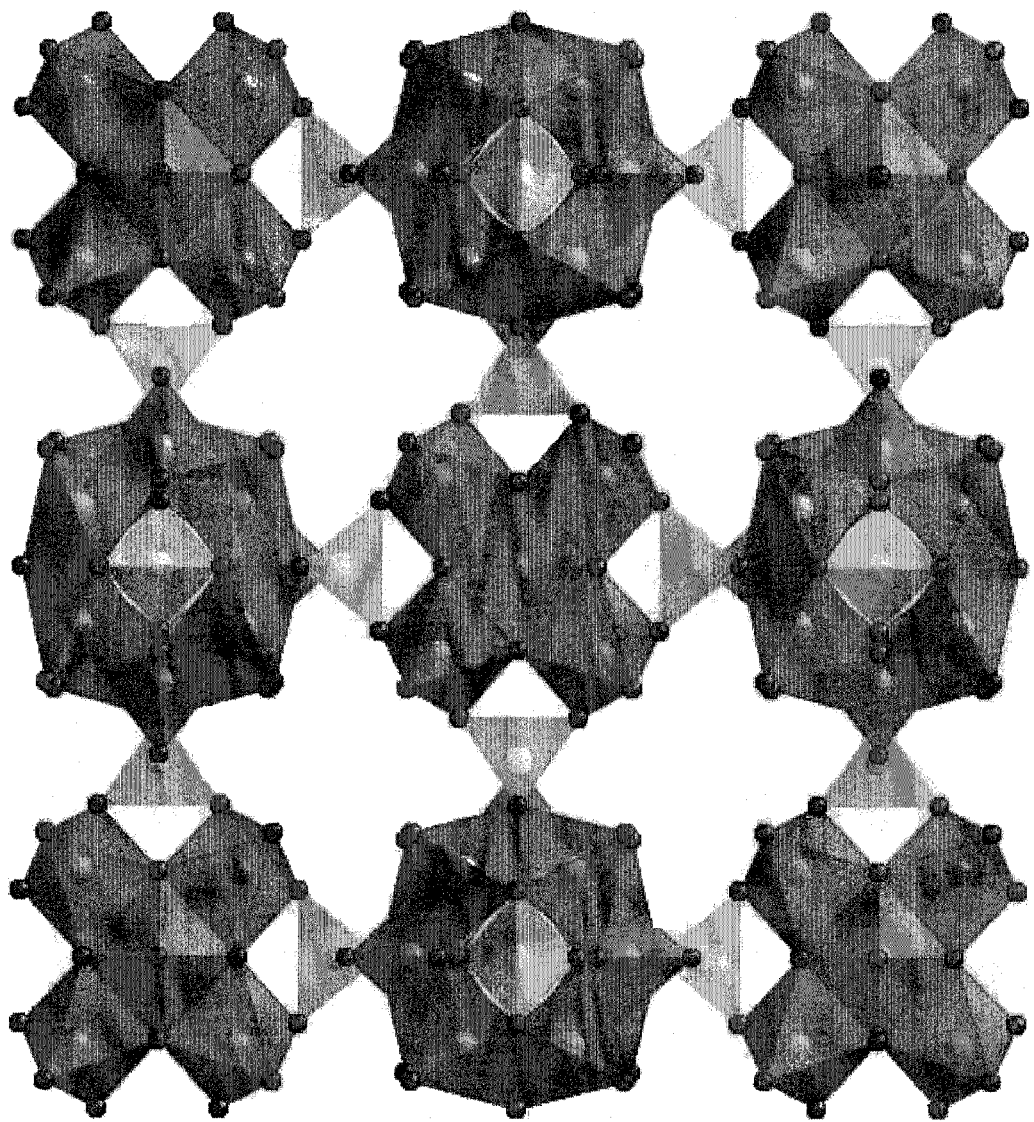
FIG. 1A is an illustration of a vanadium arsenate framework of the present invention as shown looking down the crystallographic a axis. Tunnels run along the a, b and c axes of the cubic structure. Intersections of the tunnels yield pores (see FIG. 1B). Extra-framework constituents are removed for clarity. Dark gray polyhedra represent vanadium, while light gray tetrahedra represent arsenic. The spheres represent oxygen.

The following words and phrases are used in this specification as defined below.

"Microporous" is used in its common meaning and refers to materials having pore diameters less than 2 nm.

"Mixed conductor" is used in its commonly understood meaning and refers to a material in which both electronic conduction and ionic conduction contribute to electrical conductivity.

"Oxo-vanadium arsenate" has the same meaning as "vanadium arsenate."

"Zeolites" are microporous, aluminosilicate materials where the framework is formed by Al and Si tetrahedra and where the framework delineates channels and/or tunnels that may intersect to yield cavities and pores that house extra-framework constituents.

"Zeotype materials," while not aluminosilicates, are similar to zeolites wherein a framework delineates channels/tunnels and cavities and pores that house extra-framework constituents. In both zeolites and zeotypes, the extra-framework constituents present as part of the synthesis step may be exchanged after the initial synthesis step with other ions/molecules.

In general embodiments of the present invention, there are provided compositions that may act as mixed conductors, including microporous mixed conductors; vanadium arsenate mixed conductors, vanadium phosphate mixed conductors, and mixed conductors including a framework (such as, e.g., a vanadium arsenate framework) which shows electronic conduction. The compositions of the present invention may also include a set of extra-framework constituents (such as, e.g., extra-framework constituents comprising an organic template and water; extra-framework which can be exchanged; etc.) which show ionic conductivity. Preferred examples of the compositions of the present invention are microporous vanadium arsenate and a microporous vanadium phosphate, with microporous vanadium arsenate more preferred.

In embodiments of the invention where a vanadium arsenate framework is used, an organoammonium template may be used as an organic template, forming a mixed conductor. In certain embodiments, the organoammonium template is piperazine. It is also contemplated that other organic templates besides organoammonium templates, which produce electrically conducting vanadium arsenate, may be used. In embodiments of the invention where a vanadium phosphate framework is used, methenamine may be used as an organic template, forming a mixed conductor. It is also contemplated that other organic templates, besides methenamine, which produce an electrically conducting vanadium phosphate, may be used.

For the microporous materials of the present invention, preferably the microporous material has pore sizes ranging from about 0.3 nm to about 0.7 nm, more preferably pore sizes of about 0.5 nm. However, it is also contemplated that the microporous materials may have smaller or larger pore sizes. The term pore size, as used herein, may be applied interchangeably to the size of tunnels and cavities in the compositions of the present invention, and these size ranges also apply to tunnels and cavities as presented herein.

In certain embodiments of the compositions of the invention, the compositions are crystalline vanadium compositions that include, as determined by x-ray diffraction, a three-dimensional covalently-bonded framework made up of $VO_5$ polyhedra, $VO_6$ octahedra and $AsO_4$ tetrahedra. The connectivity of the covalently-bonded three-dimensional framework generates tunnels and cavities that may have a size range of about 0.3 nm to about 0.7 nm. In other embodiments of the present invention, the $AsO_4$ tetrahedra may be replaced with phosphate tetrahedra.

It is contemplated that the compositions of the present invention may have frameworks that contain defects in their structure, e.g. frameworks that have deviations from a perfect crystal structure. These defects may arise during the normal synthesis process. It is recognized that these defects may affect the conductivity of the frameworks of the compositions of the present invention.

The tunnels and cavities of the compositions of matter of the present invention may house organic cations and/or water molecules. Organic cations that are contemplated include cyclic di- or multi-amines, di- or multi-amines, or amines (e.g., NH—$(C_nH_{2n})_x$—NH), $NH_2$—R—$NH_2$, or R—$NH_2$, where R may be an alkyl or an aryl group). In certain embodiments, when the composition includes $AsO_4$ tetrahedra, the organic cation is piperazine. In certain other embodiments, when the composition includes phosphate tetrahedra, the organic cation is methenamine.

It is also contemplated that the tunnels and cavities of the compositions of the matter of the present invention may house inorganic cations such as $Li^+$, $Na^+$, $K^+$, $Rb^+$ and $Cs^+$. Organic cations in the framework may be exchanged through intercalation reactions where single crystals or pressed powder pellets of the compositions of the present invention are placed in aqueous salt solutions containing the inorganic cation of interest. It is further contemplated that the tunnels and cavities of the compositions of the present invention may house both organic and inorganic cations within the same composition.

In another embodiment of the complexes of the present invention, the complexes are represented by Formula I:

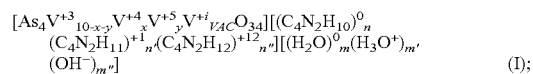

(I);

where VAC is a vacancy and where $0<x<9$; $0<y<9$; $0<VAC<1$, where x, y and VAC each can be an integer or non-integer; +i is +3, +4 or +5, where $0<n<6$; $0<n'<6$; $0<n''<6$ where n, n' and n'' each can be an integer or non-integer; and where $0<m<24$; $0<m'<24$; $0<m''<24$ where m, m' and m'' each can be an integer or non-integer.

In certain embodiments of the invention, the complexes are represented by Formula I where $7<x<9$, $1<y<3$, VAC is 0, the summation of n, n' and n'' is between 4.5 and 5.5 and the summation of m, m' and m'' is between 12 and 18.

As with the embodiments described above, the tunnels and cavities of Formula I may house organic and/or inorganic cations.

In another embodiment, the compositions of the present invention are vanadium oxide arsenate compositions having been characterized by a framework having a generic formula characterized by Formula II:

(II);

where VAC means a vacancy and where $0<x<9$; $0<y<9$; $0<VAC<1$, where x, y and VAC each can be an integer or non-integer; and +i is +3, +4 or +5.

In this embodiment, the tunnels and cavities of the framework formed by Formula II may house inorganic and organic cations as is described above. In a preferred embodiment, the framework formed by Formula II houses piperazine or piperazinium cations and water molecules.

In yet another embodiment, the compositions of the present invention are represented by Formula III:

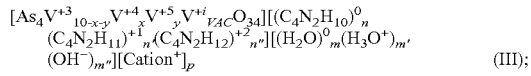
(III);

where $0<n$, n', $n''<1$, $1<p<12$, and $0<m$, m', $m''<16$.

In this embodiment, some or all of the organic cations have been replaced by inorganic cations, as is described above.

Figure 1B:
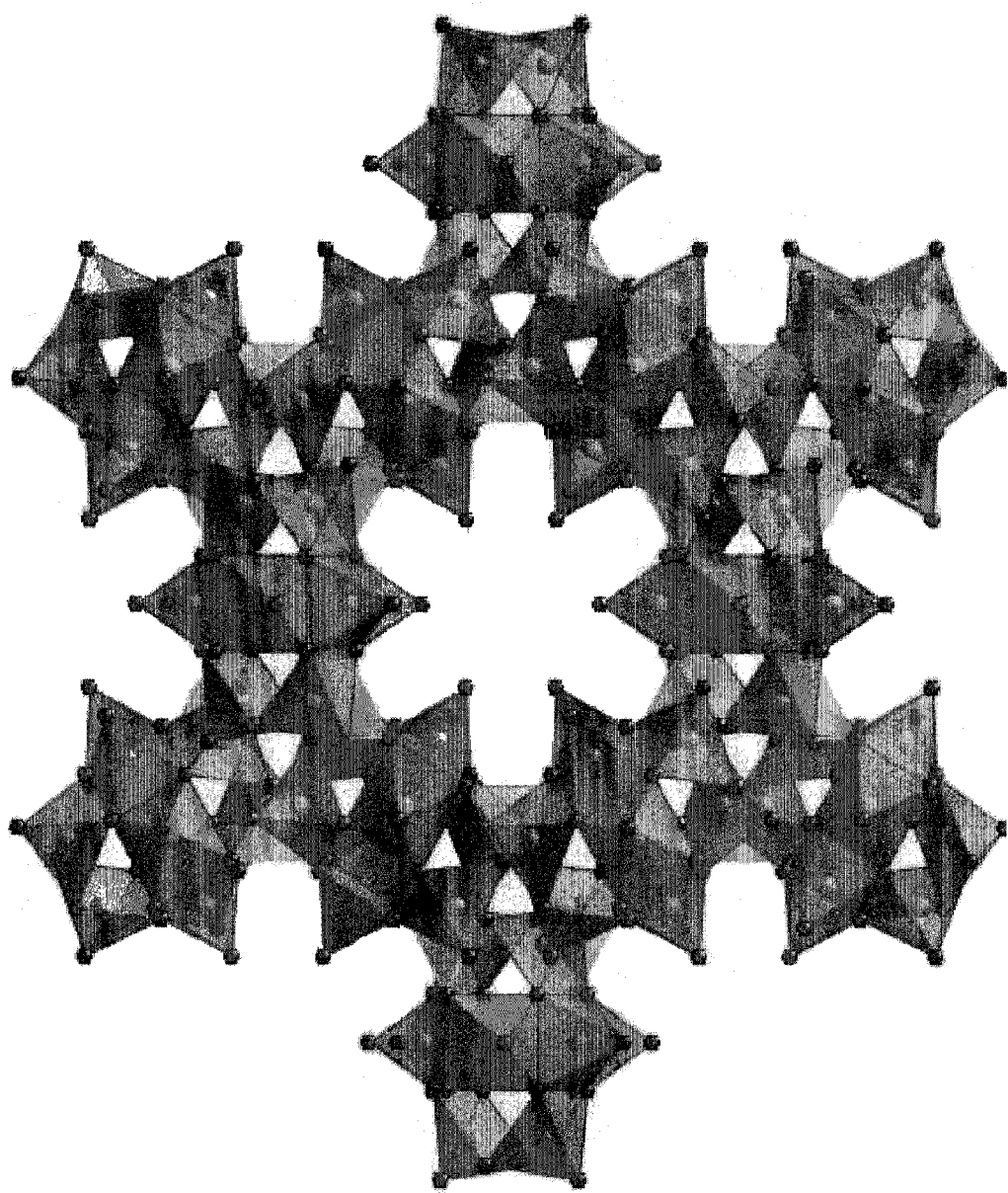
FIG. 1B is an illustration of a vanadium arsenate framework of the present invention as shown down the 111 direction. The accessible pore, e.g. the pore size which allows ions/molecules to enter and leave the framework, is on the order of 0.5 nm. The void space is larger than the accessible pore space. Extra-framework constituents are removed for clarity. The color scheme is the same as for FIG. 1A.

By way of example only, a structural representation of an electrically conducting vanadium arsenate structure of the present invention, obtained from single crystal x-ray diffraction, is shown in FIGS. 1A and 1B. The structure is shown looking down the crystallographic a axis (FIG. 1A), as well as looking down the 111 direction (FIG. 1B). The structure crystallizes in a cubic space group, and a preferred embodiment is for the structure to be solved in the space group Im $\bar{3}$m.

A preferred example of a microporous framework for use in the invention is a microporous framework that can intercalate various other ions and or molecules into the framework, such as, e.g., alkali, alkali earth, metal cations, amines, di or multi amines, cyclic mono di or multi amines, and alcohols.

The frameworks of the present invention will possess favorable electrical properties which can be characterized using techniques well known in the art. Certain, non-limiting examples of techniques which can be used can be found in the Examples set forth below. An example of electrical characterization is the dependence of resistance on the temperature of the framework and any constituents present.

Without wishing to be bound by theory, the compositions of the present invention may demonstrate mixed conductivity, e.g. both ionic and electronic conductivity. For example, there may be constructed a vanadium arsenate that is a mixed conductor having electronic conductivity due to the vanadium arsenate framework and ionic conductivity due to organic cations and water housed inside the tunnels and cavities.

The present invention also contemplates methods for the synthesis of the compositions of the present invention. In preferred embodiments, the reagents used in the synthesis of the compositions of the present invention include at least one organic template (such as, e.g., cyclic di- or multi amines, di or multi-amines, or amines (e.g., NH—$(C_nH_{2n})_x$—NH), $NH_2$—R—$NH_2$, or R—$NH_2$), at least one vanadium source (e.g. V, $V_2O_3$, $NH_4VO_3$, $NaVO_3$, $KVO_3$), at least one tetrahedral linker (e.g., $PO_4$, $AsO_4$), and/or at least one metal cation (e.g., alkali or alkali earth metals), and/or an acid source. Preferably the synthesis method uses a solution based route, and may be a hydrothermal synthesis or a solvothermal synthesis. The reaction mixture may be incubated at about 373 K to about 513 K for a period of 42 to 108 hours. However, shorter or longer reaction periods are also contemplated. In certain embodiments where an arsenate composition is formed, the temperature is 453 K. In certain embodiments where a phosphate composition is formed, the reaction temperature may be about 473 K.

In certain methods of the present invention, vanadium arsenate compositions are synthesized using a reaction mixture having reagents in the following molar ratios:

| $V_2O_3$ | $As_2O_5$ | piperazine ($C_4H_{10}N_2$) | HCl | $H_2O$ |
|---|---|---|---|---|
| 1 | 0.941-0.985 | 1.674-2.413 | 1.147-3.462 | 653-870 |

In certain other methods of the present invention, vanadium arsenate compositions are synthesized using a reaction mixture having reagents in the following molar ratios:

| $V_2O_3$ | V | $As_2O_5$ | piperazine | HCl | $H_2O$ |
|---|---|---|---|---|---|
| 1 | 0.275-0.290 | 1.05-1.2 | 2.95-3.12 | 3.20-3.30 | 1000-1150 |

In certain other methods of the present invention, vanadium phosphate compositions are synthesized using a reaction mixture having reagents in the following molar ratios:

| $NH_4VO_3$ | $H_3PO_4$ | methenamine | $H_2O$ |
|---|---|---|---|
| 1 | 1.144 to 1.146 | 1.71 to 1.72 | 260 to 285 |

Although other synthesis processes are contemplated, in certain embodiments, the vanadium and arsenate oxides are added to the reaction mixture first, followed by organic template, hydrochloric acid and then water. In other embodiments, piperazine and HCl are added first with some of the water, followed by V and $V_2O_3$, and then $As_2O_5$. However, other methods which involve the addition of reagents in different orders are also within the scope of the present invention.

The crystalline structures of the compositions of the present invention may be determined using techniques well known in the art, such as by single crystal x-ray diffraction. Other properties of the compositions may also be measured, such as an elemental analysis, infra-red spectra, thermogravimetric analysis, and other tests for other properties as are known in the art.

In other embodiments, the present invention provides electrical energy storage media containing the electrically conducting zeolite-like frameworks of the invention. Electrical energy storage (such as, e.g., ultracapacitors); energy applications (e.g. in ion-exchange membrane technologies and catalysis); and other uses are contemplated by the invention.

The compositions of the present invention may significantly improve a wide variety of areas such as charge storage applications, chemical catalysis, adsorption, separation reactions, etc. As an electrically conducting framework possessing high pore density per unit volume and uniform pore size distribution, the compositions of the present invention can provide greater energy density for capacitors, ultracapacitors, battery electrodes, and ion conducting membranes. Manipulating the charge state of these compositions also creates an electrically active framework useable to control catalytic, adsorption, or separation processes. The compositions are also useful for novel memory and electronic and/or optoelectronic devices.

The compositions of the present invention can be formed into various shapes such as films and pellets formed of pressed powder. The powder form of the material may be pressed into a form with the help of a press as is well known in the art, typically through the application of mega- to giga-Pascals of pressure. The pressed shape may be varied as is well known in the art. The powdered form of the compositions of the present invention may also be pressed on a flexible or solid substrate as is well known in the art, e.g. through screen printing type applications. In certain embodiments, a pressed film can be formed, the film can then be electrically contacted, and then the whole device encapsulated. Typically, and is well known in the art, the film may be bottom contacted with encapsulation from the top to minimally impact device characteristics.

The following examples are meant to illustrate some of the embodiments of the present invention and should not be considered to limit the scope and spirit of the invention as is set forth in the claims below.

EXAMPLES

Example 1

Electrically Conducting Vanadium Arsenate Microporous Frameworks

The synthesis and characterization of a novel microporous material with electrically conducting properties is shown. This inventive example is distinct from existing microporous or zeotype materials which are electrically insulating. This new material can significantly improve a wide variety of areas such as charge storage applications, chemical catalysis, adsorption, separation reactions, etc. As an electrically conducting framework possessing high pore density per unit volume and uniform pore size distribution, the material described in this example can provide greater energy density for capacitors, ultracapacitors, battery electrodes, and ion conducting membranes. Manipulating the charge state of this material also creates an electrically active framework useable to control catalytic, adsorption, or separation processes. This material also is useful for novel memory and electronic and/or optoelectronic devices.

In this example, a novel organically templated vanadium arsenate was synthesized and characterized. The material is a microporous zeotype framework, and the organic templates and water molecules are expelled from the framework under a thermal treatment, as ascertained by thermogravimetric analysis. The framework is capable of exchanged reactions, where template/water is exchanged for various ions.

The electronic properties of the material were investigated. The as synthesized, thermally treated and ion exchanged frameworks all show electronic characteristics that may be exploited for various applications ranging from electrical double layer capacitors, battery electrodes, catalysis, etc.

A vanadium arsernate composition was synthesized using hydrothermal methods. Vanadium oxide, arsenic pentoxide, piperazine organic template hydrochloric acid and water were combined in the following ratios:

| $V_2O_3$ | $As_2O_5$ | piperazine | HCl | $H_2O$ |
|---|---|---|---|---|
| 1 | 0.941-0.985 | 1.674-2.413 | 1.147-3.462 | 653-870 |

Optimal yields were obtained when the reactants were reacted at 433 K to 473 K, at a time duration ranging from 2.5 days to 4.5 days. The preferred reaction temperature and times were 453 K and for 3 to 3.75 days. The yield was influenced by temperature, time duration and reactant ratios.

The order of addition also influenced the yield of the zeotype material, which, under optimal conditions achieved so far in this example, was the major product. The optimal order was the V and As oxides first, then the template, HCl, and finally, the water.

The vanadium arsenate of this example may also be formed as the dominant product (the percent yield based on vanadium starting material is in the range of 85 to 90%) when the reactant ratios shown below are reacted using hydrothermal synthesis. Vanadium oxide, vanadium metal, arsenic pentoxide, piperazine organic template, hydrochloric acid and water were combined in the following ratios:

| $V_2O_3$ | V | $As2O_5$ | piperazine | HCl | $H2O$ |
|---|---|---|---|---|---|
| 1 | 0.275-0.290 | 1.05-1.2 | 2.95-3.12 | 3.20-3.30 | 1000-1150 |

Optimal yields were obtained when the reactants were reacted at 433 K to 473 K, at a time duration ranging from 2.5 days to 4.5 days. The preferred reaction temperature and times were 453 K and for 3 to 3.5 days.

A zeotype with the desired electrical characteristics did not form without the organic template present. Also, other sources of vanadium and arsenic did not, in this example, yield this particular zeotype. Importantly, the presence and amount of HCl appeared to be crucial. The zeotype material can be distinguished from other minor products as a dark colored cubic crystal.

The composition was tested as follows.

Microprobe analysis and elemental analysis confirmed the presence of C, H, N, V, and As in the synthesized product (oxygen content is obtained by difference). Infrared spectrum analysis showed characteristic frequencies associated with the organic template molecule and the water molecule. Thermogravimetric analysis indicated ease of loss of template and water ions from the framework. Single crystal X-ray diffraction indicated the reproducibility of the reaction conditions. The framework was found to be stable up to 770 K, and the template and water ions present in the as-synthesized material could be exchanged with other cations.

Figure 2A:
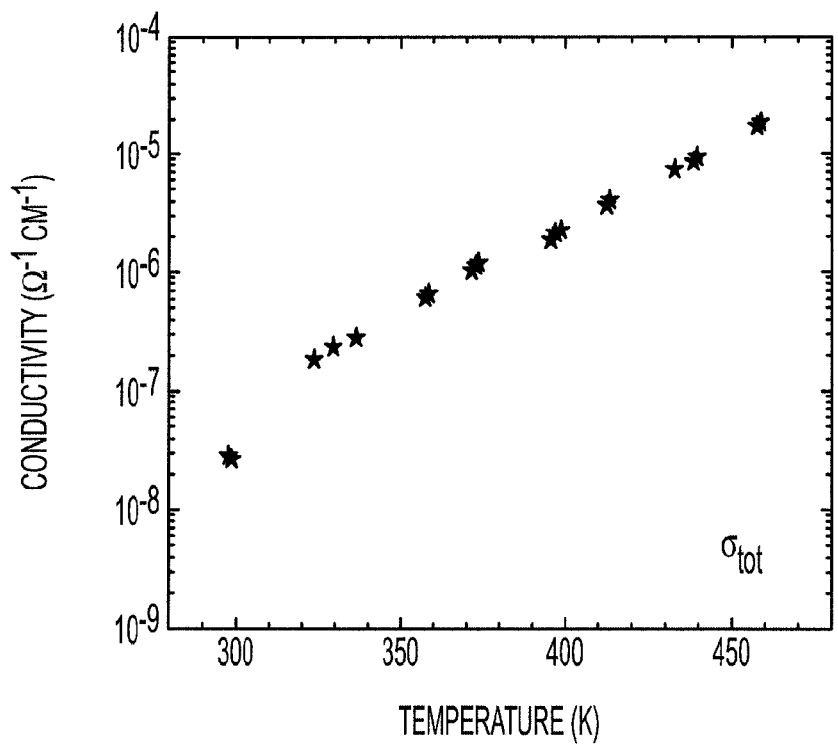
FIG. 2A is a graph of conductivity as a function of temperature for the composition of Example 1, showing conductivity of the as-synthesized material consisting of the framework with the extra-framework constituent template or ions.
Figure 2B:
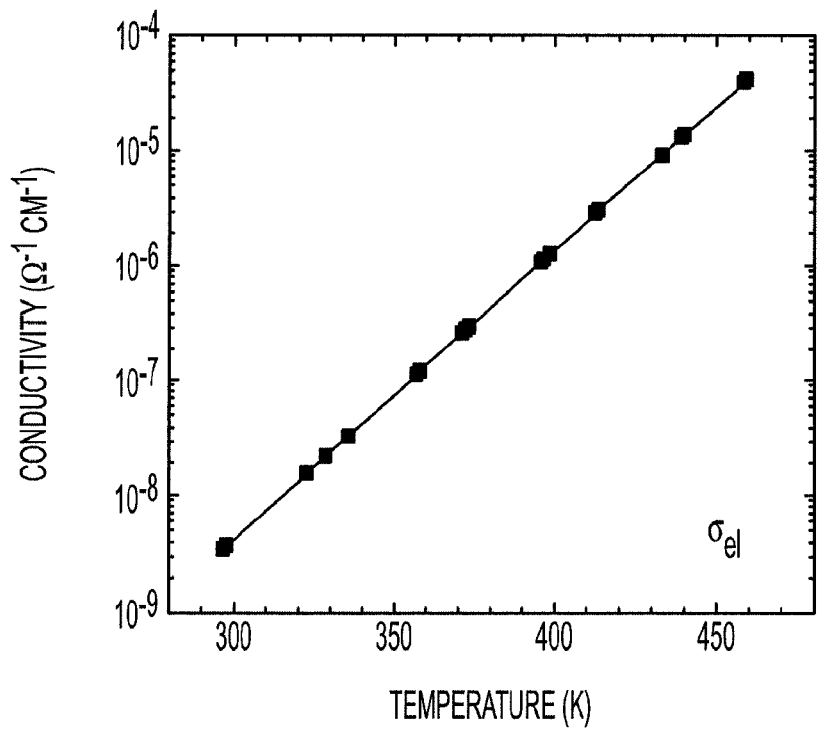
FIG. 2B is a graph of conductivity as a function of temperature for the framework only after thermally treating the composition of Example 1 at 573K under a flow of $N_2$ gas. Further details are provided in Example 1.
Figure 2C:
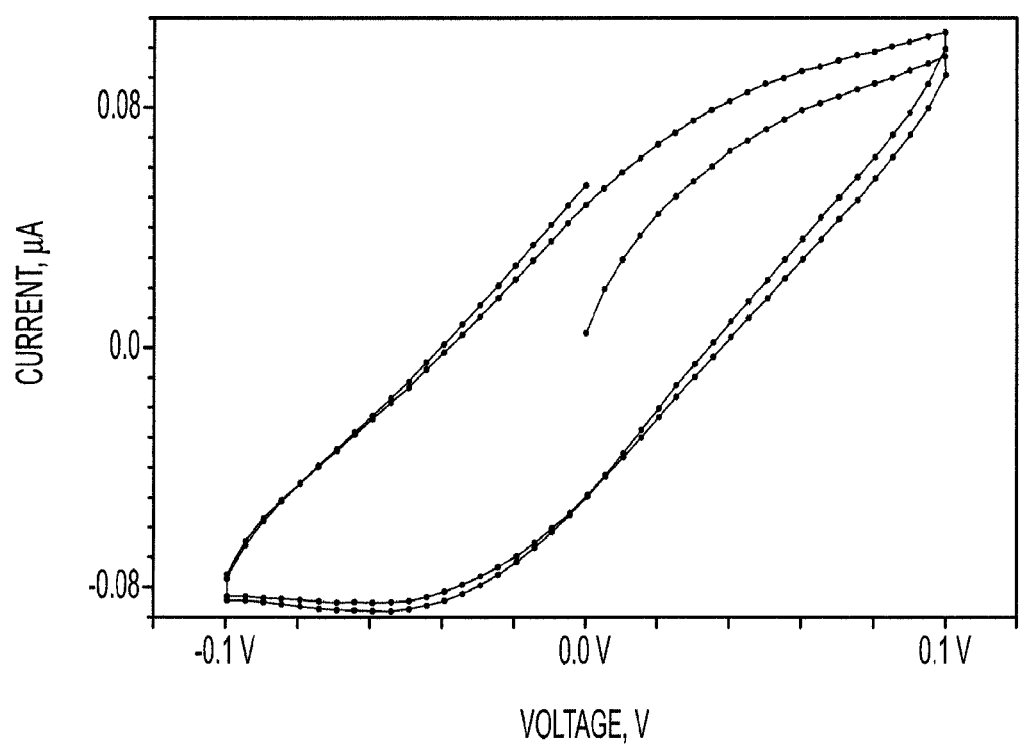
FIG. 2C is an current-voltage (I-V) curve of the K+ intercalated zeotype for the materials of Example 1. Further details are provided in Example 1.

Uniquely, the zeotype material of Example 1 exhibited electronic conducting properties. FIGS. 2A, 2B and 2C show the changes in the electronic properties for the as-synthesized material (FIG. 2A), thermally treated material (FIG. 2B) e.g. framework only, and material intercalated e.g. with K+ (FIG. 2C). The K+ exchanged framework shows interesting electrochemical characteristics and useful properties for e.g., electrodes.

Current-voltage (I-V) curves (FIGS. 2A and 2B) were obtained on single crystals with two contacts, and resistance values measured. Resistivity was calculated based on the resistance values measured and the sample dimensions. Typical sample dimensional were cubes with a side of 50 micrometer. Conductivity values were obtained from the resistivity values.

Samples were thermally treated to 573 K under a flow of $N_2$ gas. The thermal treatment expels the organic template and water molecules out of the framework. The temperature of the thermal treatment was chosen from the thermogravimetric analysis data. I-V curves were obtained on single crystals with two contacts, and conductivity values extracted from the data. Samples were measured before thermal treatment, and the conductivity before heating was roughly 20 times greater than after heating.

FIG. 2C is a solid-state voltammogram of the framework for the material of Example 1 exchanged with K+; the data were obtained on single crystals with two contacts. Samples were measured before and after soaking in concentrated KCl solution to exchange the organic template with K+. Data not shown. Two vanadium arsenate crystals, intercalated with KCl and placed in an electrolyte of KCl at a separation of 10 mm, and current-voltage measurements obtained. Measurement starts at 0 V→+0.1 V→0.1 V, etc. Data were taken at ~300 K.

The synthesized zeotype framework of this Example shows temperature activated electrical conduction. Exchange reactions, e.g., with alkali cations, show that certain ions can efficiently replace template molecules used in the synthesis of the inventive framework. Further, the exchanged frameworks sustain ion conduction. Applications for uptake, conduction and release of ions include, e.g., ultracapacitors of high energy density and battery technology. The conducting exchanged zeotype shows electrochemical reactions occurring on the ions under applied potential, where the framework functions as an electrode. That capability is useable in electrically controlled catalysis, in electrically activated separation, and in battery technology.

The zeolite-like materials of the present Example present high effective area, due to the unusually dense and regular network of channels and pores defined by the crystal structure. Pore dimensions in microporous zeolites are influenced by the synthetic conditions, allowing control over the pore size and its distribution. The double-layer concept carries over to a zeolite-like material. A positive charge residing in a zeolite pore may induce a distribution of compensating charges from electrons in a framework (such as a framework shown in FIGS. 1A and 1B). In this example, the double-layer separation is, as usual, atomic in scale, leading to high capacitance in this geometry. However, for zeolite-like materials to serve as EDLC charge storage units, a framework is needed that supports electronic conductivity such as an oxo-vanadium arsenate zeolite-like material.

The oxo-vanadium arsenate of this Example was synthesized through hydrothermal methods. The 3-dimensional framework of this material, as obtained by single crystal x-ray diffraction, is depicted in FIGS. 1A and 1B, and delineates channels that run down the 3 crystallographic directions. Extra-framework constituents, here the organic template organoammonium cation, and water (omitted from the figure for clarity), are situated in the channels which intersect along the diagonals of the cube. The framework shown in FIGS. 1A and 1B is generated from idealized coordinates for the framework atoms in the space group Im$\bar{3}$m. The structure exhibits disorder potentially influencing the measured electrical characteristics. The presence of the organic template is crucial for the isolation of this particular material. The material was microporous, with accessible pore dimension of 0.5 nm. The extra-framework constituents within the pores of the as-synthesized material were removable by heating under an inert atmosphere or through intercalation reactions. Thermogravimetric analysis indicates the temperatures at which the extra-framework constituents were expelled, recorded as a loss in weight of the sample. Weight loss started around 340 K, and by 370 K a considerable weight loss had occurred, attributed to the loosely held water inside the pores. A second weight loss occurred around 470 K, and a third around 600 K, attributed to tightly held water and the organoammonium template inside the pores, respectively. Above 600 K, the framework pores were void, leaving an empty framework which was stable up to 770 K.

Figure 3:
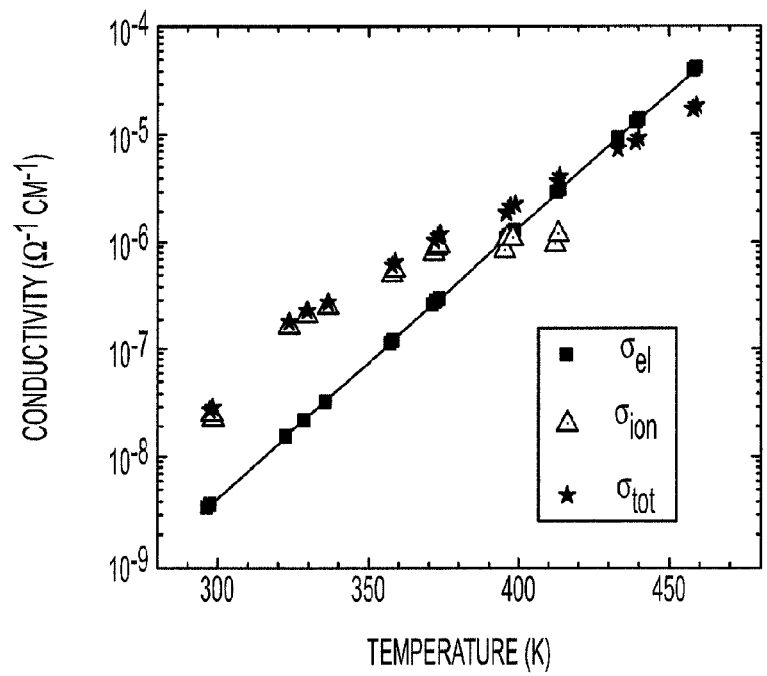
FIG. 3 is a plot of various σ, as log (σ) vs T for the compositions described in Example 1. σion represents ionic conductivity, σel represents electronic conductivity, and σtot represents total conductivity.

The zeolite-like material in this example exhibited mixed conductivity: ionic due to the extra-framework constituents, and electronic due to the framework. We investigated the contributions and interplay of the parallel ionic and electronic conduction pathways through measurement of the electrical conductivity ($\sigma$) as a function of temperature (T). Conductivity values are obtained from electrical resistance measurements on single crystals contacted with silver epoxy. The measured room temperature conductivity of a cube with 50 μm edge is $\sigma = 3.3 \times 10^{-8}$ Ohm$^{-1}$ cm$^{-1}$. The contribution of the ionic conductivity ($\sigma$ion) may be obtained by subtracting the electronic conductivity ($\sigma$el) due to the empty framework from the total conductivity ($\sigma$tot), because both the parallel electronic and ionic conductivities contributed to $\sigma$tot, attributable respectively to the framework and the extra-framework constituents (here water plus organoammonium ions). We plotted the various $\sigma$, as log ($\sigma$) vs T (FIG. 3). Initially, $\sigma$ion (triangle) increased as T increased, but, around 380 K, the trend leveled off. Indeed, $\sigma$ion was influenced by the loss of extra-framework ions resulting in a decrease in protonic conduction and a hydration dependent change in ion mobility. Deriving reliable values of $\sigma$ion above 380 K was further influenced by the fact that at higher T, $\sigma$el eventually dominated $\sigma$tot. Reliable measurements of $\sigma$ion extended to 420 K only, although $\sigma$ion was obtained up to 465 K. In short, for T>380K, the measured $\sigma$tot was dominated by the electronic contribution, while at low T, $\sigma$tot was dominated by the ionic contribution. The decrease in water and organoammonium ions at the higher T influenced $\sigma$el, as $\sigma$el then, within the accuracy of the data, increased above the value obtained for the full framework. Hence, both conduction mechanisms were interdependent, as expected if the presence of extra-framework ions led to more localized electronic states, reducing the mobility.

To access electronic transport, measurements were performed on the empty framework, namely material where the extra-framework constituents were expelled from the pores under a thermal treatment. As mentioned above, when the material was heated up to 600 K, the extra-framework constituents—here water plus organoammonium—were expelled yielding an empty framework. The framework was back-filled with $N_2$, and kept under an overpressure of $N_2$, to avoid reoccupation of the channels with water for subsequent measurements. We observed $\sigma$el increasing exponentially with increasing T, indicative of non-metallic conduction. The T dependence did not follow standard expressions for 1-, 2- or 3-dimensional Mott variable range hopping, or for activation across an energy gap, excluding these known mechanisms of electron transport even when accounting for the effective dimensionality (1, 2, or 3) of electron dynamics in the framework. Electronic conductivity in the material is likely influenced by coupling to the ionic degrees of motion, with polaron-like contribution.

Figure 4:
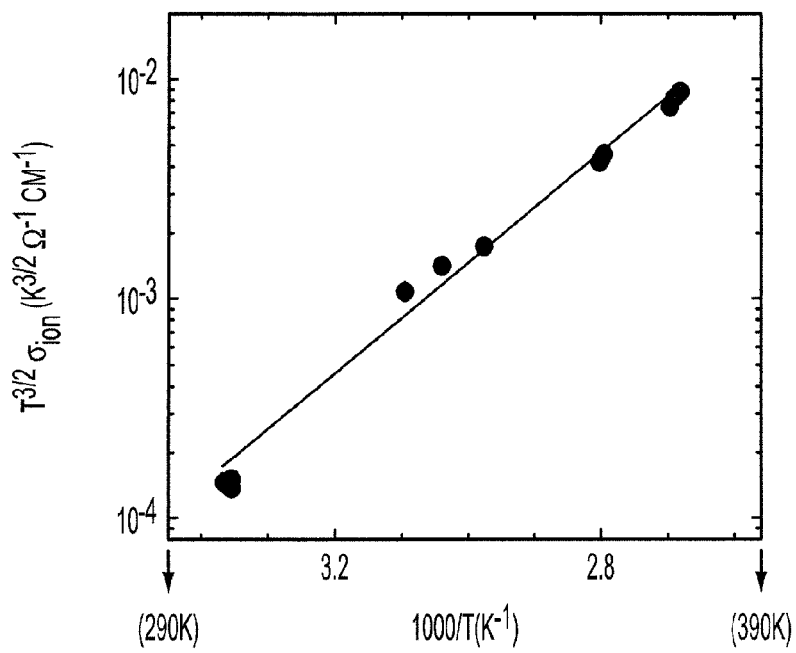
FIG. 4 is a plot of $T^{3/2}$ σion vs. 1000/T, measuring the σion contribution versus temperature as is further described in Example 1.

Next, we investigated the ionic contribution, defined as $\sigma$ion=$\sigma$tot−$\sigma$el. For the T dependence of $\sigma$ion, we plotted data up to 420 K. Above 380 K, $\sigma$ion saturated to a near constant value, as extra-framework constituents (water plus organoammonium) are expelled from the framework. A simple Arrhenius-activated model of ionic transport did not fit well. A better fit was obtained upon considering channeling of ions through a sublattice of attachment sites in the framework, through a mechanism that at least includes phonon-assisted hopping. Theoretically, $\sigma$ion then obeys $T^{3/2}$ $\sigma$ion $\propto \exp(-E_A/k_BT)$, where $E_A$ denotes a characteristic activation energy required for ion hopping from attachment site to attachment site (see FIG. 4). This relation was borne out experimentally with $E_A \approx 0.50$ eV, and indeed physically led to an acceptable picture of ion conduction in zeolite-like materials, where channels and attachment sites can be identified within the framework.

The vanadium framework of this example was robust towards intercalation. The organoammonium cation was exchangeable with inorganic cations, and e.g., the K+ exchanged framework exhibited no change in its crystalline framework as determined by single crystal x-ray diffraction. The robustness of the framework, coupled with the electronic characteristics observed, yield a good candidate for EDLC applications. In a capacitor, the stored energy U is expressed by $U=\frac{1}{2}CV^2=\frac{1}{2}QV$, where C is the capacitance, Q the stored charge and V the voltage. A high Q per material volume is an advantage, realized by the high pore density in a zeolite-like material. Equivalently, U increases when C increases, and a high C is realized in zeolite-like EDLCs by the electrical double-layer storage and high effective area. Thus an electrically conducting zeolite-like material would provide favorable U (i.e., substantially-increased).

Figure 5:
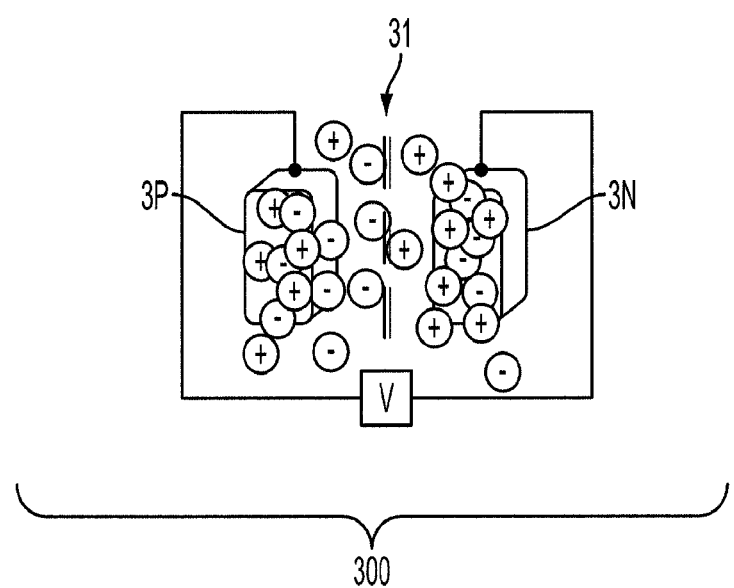
FIG. 5 is a diagram of an EDLC comprising two zeolite-like frameworks.

Referring to FIG. 5, which is a schematic diagram of an EDLC 300, the two frameworks 3P, 3N in this Example are two conducting vanadium arsenate frameworks attached to an external voltage source V. An ion membrane 31 is located in-between, permeable to the electrolyte ions. Framework 3P is positively charged and hosts negative ions inside its structure. Framework 3N is negatively charged and hosts positive ions inside its structure. In series, frameworks 3P, 3N form a storage capacitor ½ C. Charging and discharging in principle does not consume material, promising the many charge-discharge cycles inherent in the capacitor concept. Preliminary calculations of energy stored in this vanadium arsenate structure indicate a factor of 5 to 8 increase in Q and C per material volume over mesoporous carbon (Pandolfo and Hollenkamp, J. Power Sources, 157, 11 (2006); Huang, et al., Angew Chem., Int. Ed. 47, 520 (2008)). Indeed, the effective area per unit volume of material, α, is approximated by $\alpha=6p/D$ where p denotes the fraction of pore volume to total material volume and D denotes the average pore diameter. In the microporous vanadium arsenate with a pore diameter of 0.5 nm, p is higher and D is smaller than in mesoporous carbon, resulting in a substantial increase in C and Q. Preliminary capacitance measurements validate the calculated ~8-fold increase.

Example 2

Electrically Conducting Vanadium Phosphate Microporous Frameworks

A vanadium phosphate composition was synthesized using hydrothermal methods. Ammonium vanadate, phosphoric acid, methenamine organic template and water were combined in the following ratios:

| $NH_4VO_3$ | $H_3PO_4$ | methenamine | $H_2O$ |
|---|---|---|---|
| 1 | 1.144 to 1.146 | 1.71 to 1.72 | 260 to 285 |

Optimal yields were obtained when the reactants were reacted at 473 K, at a time duration ranging from 42 to 54 hours.

The vanadium phosphate composition synthesized in this Example was measured and showed an electronic) conductivity lower than that of the arsenate composition of Example 1 by a factor of about 1.2 to about 1.7.

What is claimed is:

1. A composition of matter having Formula I:

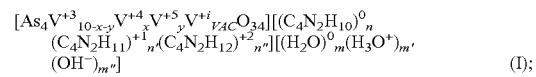

(I);

wherein VAC is a vacancy; $0<x<9$; $0<y<9$; $0<VAC<1$, wherein x, y and VAC each is an integer or non-integer; +i is +3, +4 or +5; $0<n<6$; $0<n'<6$; $0<n''<6$; wherein n, n' and n'' each is an integer or non-integer; and wherein $0<m<24$; $0<m'<24$; $0<m''<24$, wherein m, m' and m'' each is an integer or non-integer.

2. The composition of matter of claim 1, wherein $7<x<9$, $1<y<3$, VAC is 0, the summation of n, n' and n'' is between 4.5 and 5.5 and the summation of m, m' and m'' is between 12 and 18.

3. A vanadium oxide arsenate composition of matter characterized by a framework having a generic formula characterized by Formula II:

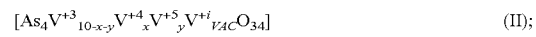

(II);

wherein VAC means a vacancy and where $0<x<9$; $0<y<9$; $0<VAC<1$, wherein x, y and VAC each is an integer or non-integer; and wherein +i is +3, +4 or +5.

4. The composition of claim 3, wherein the tunnels and cavities of the framework comprise molecules selected from the group consisting of: organic cations, inorganic cations, water molecules and combinations thereof.

5. The composition of claim 4, wherein the organic cation is piperazine.

6. The composition of claim 4, wherein the inorganic cations are selected from the group consisting of $Li^+$, $Na^+$, $K^+$, $Rb^+$ and $Cs^+$.

7. A method for synthesizing the composition of claim 1 comprising:
mixing reagents $V_2O_3$, $As_2O_5$, $C_4H_{10}N_2$, HCl and $H_2O$ to form a reaction mixture;
warming the reaction mixture to a reaction temperature; and
allowing the mixture to remain at the reaction temperature for a reaction period of time until Formula is obtained.

8. The method of claim 7, wherein the reaction temperature is between about 373 K and about 513 K.

9. The method of claim 7, wherein the reactive period of time is between about 42 and about 108 hours.

10. A method for synthesizing a composition of claim 1 comprising:
mixing reagents $V_2O_3$, V, $As_2O_5$, $C_4H_{10}N_2$, HCl and $H_2O$ to form a reaction mixture;
warming the reaction mixture to a reaction temperature; and
allowing the mixture to remain at the reaction temperature for a reaction period of time until Formula I is obtained.

11. The method of claim 10, wherein the reaction temperature is between about 373 K and about 513 K.

12. The method of claim 10, wherein the reactive period of time is between about 42 and about 54 hours.

13. An ultracapacitor containing the composition of matter of claim 1.

14. An ultracapacitor containing the composition of matter of claim 3.

* * * * *